United States Patent [19]

McCue et al.

[11] Patent Number: 5,414,170

[45] Date of Patent: May 9, 1995

[54] MIXED PHASE FRONT END $C_2$ ACETYLENE HYDROGENATION

[75] Inventors: Richard H. McCue; Edna B. Hicks, both of Houston, Tex.

[73] Assignee: Stone & Webster Engineering Corporation, Boston, Mass.

[21] Appl. No.: 60,880

[22] Filed: May 12, 1993

[51] Int. Cl.$^6$ .................... C07C 5/00; C07C 5/03
[52] U.S. Cl. .................... 585/264; 585/259; 585/265; 585/275; 585/277
[58] Field of Search ............... 585/259, 264, 265, 275, 585/277

[56] References Cited

U.S. PATENT DOCUMENTS

| | | | |
|---|---|---|---|
| 3,549,720 | 12/1970 | Wright et al. | 260/677 |
| 3,679,762 | 7/1972 | La Hue et al. | 260/677 |
| 3,679,763 | 7/1972 | Livingston | 260/677 H |
| 3,770,619 | 11/1973 | Derrien et al. | 208/255 |
| 3,793,388 | 2/1974 | Pitzer | 260/677 |
| 4,121,917 | 10/1978 | Baker et al. | 62/28 |
| 4,128,595 | 12/1978 | Montgomery | 260/677 |
| 4,347,392 | 8/1982 | Cosyns et al. | 585/259 |
| 4,571,442 | 2/1986 | Cosyns et al. | 585/261 |
| 4,762,956 | 8/1988 | Liu et al. | 585/259 |
| 5,059,732 | 10/1991 | Cosyns et al. | 585/259 |
| 5,220,097 | 6/1993 | Lam et al. | 585/809 |

FOREIGN PATENT DOCUMENTS 2525210 10/1983 France ................... C07C 7/16

*Primary Examiner*—Anthony McFarlane
*Assistant Examiner*—Nhat D. Phan
*Attorney, Agent, or Firm*—Hedman, Gibson & Costigan

[57] ABSTRACT

The present invention provides an improved process for selectively hydrogenating acetylenes in an olefin plant process stream by selectively hydrogenating the acetylenes downstream of a front end depropanizer and upstream of further separation zones such as a demethanizer and/or de-ethanizer.

16 Claims, 2 Drawing Sheets

MIXED PHASE FRONT END C$_2$ ACETYLENE HYDROGENATION

The present invention relates to a process for the hydrogenation of acetylene components in an olefin production facility.

BACKGROUND OF THE PRESENT INVENTION

The processes for converting hydrocarbons at a high temperature, such as, for example, steam-cracking or alternatively, catalytic cracking, provide unsaturated hydrocarbons such as, for example, ethylene, acetylene, propylene, butadiene, butenes, lighter compounds such as methane, hydrogen and carbon monoxide, and hydrocarbons boiling in the gasoline range. Thus, the gaseous monoolefinic hydrocarbons with two or more carbon atoms, obtained by these processes also contain an amount of hydrocarbons of greater unsaturation degree. The content of these hydrocarbons depends on the severity of the conversion treatment, but is often too low to economically justify their separation and their use as such in the petrochemical field. This is often the case of the ethylene and propylene cuts from which acetylenes must be removed.

To this end, the prior art is replete with a number of patents describing catalyst compositions for the selective hydrogenation of these compounds. Exemplary of these prior art disclosures are La Hue et al., U.S. Pat. No. 3,679,762; Cosyns et al., U.S. Pat. No. 4,571,442; Cosyns et al., U.S. Pat. No. 4,347,392; Montgomery, U.S. Pat. No. 4,128,595; Cosyns et al., U.S. Pat. No. 5,059,732 and Liu et al., U.S. Pat. No. 4,762,956.

However, in the olefins plants of the prior art, the acetylene hydrogenation reactor has been located at the back end of the plant. Accordingly, the prior art processes, such as the Acetex process of the Institut Francais du Petrol, require an external fluid solvent and must carefully regulate the hydrogen ratio, carbon monoxide content and reactor inlet temperature due to pressure sensitivities to excursions in acetylene and carbon monoxide concentrations.

Further, prior designs utilizing the acetylene hydrogenation reactor in the front end of the olefins plant have experienced operating upsets due to temperature excursions experienced during initial start up resulting from the sensitivity and activity of the fresh catalyst. Typically, front end units require multiple beds to reduce temperature rise and thus the chances of upsets.

To this end there exists in the art a need for a method to hydrogenate the acetylenes in she front end of an olefin plant process stream and overcome the difficulties of the prior art processes, as discussed above.

SUMMARY OF THE PRESENT INVENTION

An object of the present invention is to provide a method for hydrogenating the acetylenes present in the front end of an olefin production plant.

Another object of the present invention is to provide a method for acetylene hydrogenation in a olefin production plant which does not require an external fluid solvent.

Still another object of the present invention is to provide a method for acetylene hydrogenation in an olefin production plant which has reduced sensitivity to excursions in acetylene and carbon monoxide concentrations, as well as depropanizer upsets.

A further object of the present invention is to provide a method for front end acetylene hydrogenation in an olefin production plant which has reduced sensitivity to temperature excursions experienced during initial start up resulting from the sensitivity and activity of the fresh catalyst.

A still further object of the present invention is to provide a method for acetylene hydrogenation in an olefin production plant which has improved safety.

A still another further object of the present invention is to provide a method for acetylene hydrogenation in an olefin production plant which has improved acetylene hydrogenation selectivity.

Yet still another object of the present invention is to provide a process having reduced sensitivity to temperature upset which employs only a single mixed phase reactor and a small vapor phase cleanup system.

DETAILED DESCRIPTION OF THE PRESENT INVENTION

The present invention provides a method for hydrogenating acetylenes present in the process stream of an olefin production facility. More particularly, the present invention contemplates employing a mixed phase hydrogenation reactor which is located downstream of a front end depropanizer and upstream of further separation means, such as demethanizers and de-ethanizers.

Accordingly, the present invention generally provides a process for treating a feedstream comprising butane, butenes, propane, propylene, ethane, ethylene, acetylene, methane, hydrogen, carbon monoxide and mixtures thereof, the process comprising the following steps in sequence: (i) depropanizing the feedstream to form a liquid stream comprising a majority of the C$_{4+}$ components and a vapor stream comprising a majority of the C$_3$ and lighter components; (ii) selectively hydrogenating the acetylene component in the vapor stream in a mixed phase hydrogenation zone; and (iii) further separating the components present in the effluent from the mixed phase hydrogenation zone.

Surprisingly, the present inventors have found that by selectively hydrogenating the acetylene downstream of the front end depropanizer and upstream of further separation means, the front end depropanizer can be used to provide the liquid wash and cooling affect for the mixed phase acetylene hydrogenation reaction. Accordingly, the mixed phase acetylene hydrogenation is inside the heat pump circuit of the front end depropanizer.

In this manner, the present inventors have unexpectedly found that the number of front end hydrogenation reaction units to fully hydrogenate the C$_2$ acetylenes is reduced, and that the hydrogenation units are better able to tolerate excursions in carbon monoxide and acetylene concentrations, as well as depropanizer upsets. Further, in operation, the reactor simulates an isothermal reactor, providing improved hydrogenation selectivity and safety.

DESCRIPTION OF THE PREFERRED EMBODIMENTS

Figure 1:
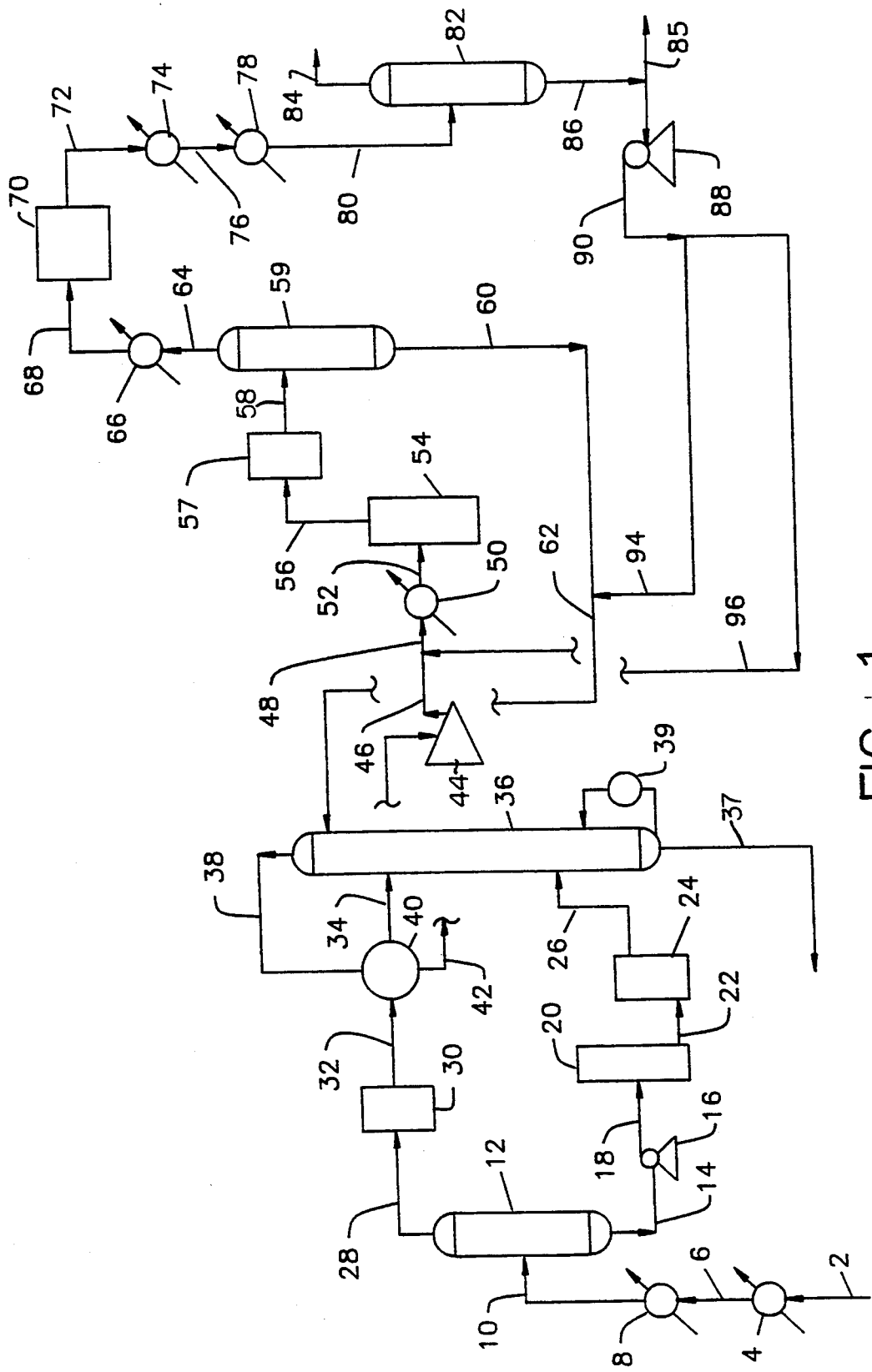
FIG. 1 depicts in flow chart format a preferred process embodiment of the present invention.

Referring to FIG. 1, a gaseous olefin containing feedstream, such as obtained from a crude oil steam pyrolysis facility, in a line 2 is cooled in heat exchanger 4 with cold water. The cooled feed in a line 6 is then further cooled and partially condensed by heat exchange with a $C_3$ refrigerant in heat exchanger 8 and fed through a line 10 to a knock out tower 12. The liquid from the knock out tower 12 containing a majority of the heavier components of the feedstream is withdrawn through a line 14, and pumped via a pump 16 through a line 18 into a coalescer 20. The liquid is which is withdrawn from the coalescer 20 is then fed via a line 22 to a drier 24, and the dried effluent is fed through a line 26 to a lower portion of a high pressure depropanizer 36.

The vapor from knock out tower 12 containing a majority of the lighter components of the feedstream is removed via a line 28 and fed to a drier 30. The dried vapor is withdrawn from the drier 30 through a line 32. The vapor in the line 32 is then indirectly heat exchanged with a vapor in line 38 (described more fully hereinbelow) and fed via a line 34 to an upper portion of the high pressure depropanizer 36.

The high pressure depropanizer 36 operates at pressures ranging from 150 psia to 300 psia and is equipped with a reboiler 39. The liquid containing substantially all of the $C_{4+}$ components and a portion of the $C_3$ components is withdrawn from the high pressure depropanizer 36 through a line 37 for further processing, such as to a downstream low pressure depropanizer.

The vapor stream containing the lighter components such as methane, ethylene, propylene, propane and acetylene, is withdrawn from the depropanizer 36 through a line 38, which is heat exchanged with the vapor stream 32 from the knock out tower 12 in a heat exchanger 40. The depropanizer vapor effluent is then directed through a line 42 to a compressor 44.

The vapor effluent in the compressor 44 is withdrawn through a line 46, mixed with a liquid recycle from a line 96 in a line 48, cooled and partially condensed in a heat exchanger 50 with cold water and directed to the mixed phase acetylene hydrogenation reactor 54 through a line 52. In this manner the front end depropanizer provides cooling and liquid wash for the mixed phase acetylene hydrogenation reactor.

The mixed phase acetylene hydrogenation reactor 54 operates at relatively low temperatures ranging from about 0° C. to about 40° C. and relatively moderate pressures ranging from about 200 psia to about 600 psia over a Group VIII metal hydrogenation catalyst, preferably a palladium-on-alumina catalyst.

The mixed-phase product effluent from the mixed-phase acetylene hydrogenation reactor 54 is withdrawn through a line 56 and directed to a knock out tower 59 via a cooler 57 and a line 58 for separation into a liquid stream and a vapor stream. The separated liquid from the knock out tower 59 in a conduit 60 rich in $C_{3+}$ components is then directed to the top of the high pressure depropanizer 36 as a reflux liquid.

The separated vapor from the knock out tower 58 is withdrawn in a line 64, heated in a heat exchanger 66, such as with steam, and directed through a conduit 68 to a vapor phase hydrogenation reactor 70.

Any catalyst well known to selectively hydrogenate acetylene can be employed in the vapor phase hydrogenation reactor 70 of the present invention. The Group VIII metal hydrogenation catalysts are the most commonly used and are presently preferred. The Group VIII metal hydrogenation catalysts are ordinarily associated with a support, such as alumina. One catalyst that has been used successfully is a low surface area granular alumina impregnated with about 0.1 weight percent palladium. Examples of other catalysts which can be used include Raney nickel, ruthenium-on-aluminum, nickel arsenide-on-aluminum, and the like and mixtures thereof. The catalysts ordinarily contain a Group VIII metal in an amount ranging from about 0.01 to about 1 percent by weight of the total catalyst. These and other catalysts are more fully disclosed in the literature.

The hydrotreating conditions employed in the vapor phase acetylene hydrogenation reactor 70 according to the present invention can vary appreciably depending upon the compositional make-up of the stream being treated. Ordinarily, the temperature and pressure will be sufficient to complete the hydrogenation of substantially all of the $C_2$ acetylenes contained in the stream fed to the vapor phase hydrogenation reactor 70. Generally, the hydrotreating process will be carried out over a temperature range of from about 10° C. to about 200° C. and a pressure range of from about 200 psia to about 600 psia. Hydrogen flow, during the hydrogenation, is at least sufficient to meet the stoichiometric requirements for converting acetylene into ethylene, and, generally, is in the range of about 1 to 100 mols of hydrogen per mol of acetylene. Reaction time can vary from about a few seconds to a few hours, and is generally in the range of from about 1 to 6 seconds. The process can be carried out employing the catalyst in a fixed bed or other type of contacting means known to those skilled in the art.

The effluent from the vapor phase acetylene hydrogenation reactor 70 is withdrawn through a line 72 and passed through a chilling train comprising heat exchangers 74 and 78 and a connecting line 76, wherein the effluent is cooled and partially condensed with a $C_3$ refrigerant. The chilled effluent in a line 80 is then directed to a knock out tower 82 for separation into a vapor stream and a liquid stream.

The vapor is removed from the knock out tower 82 in a line 84 rich in the lighter components including ethylene, methane and hydrogen, and sent to a downstream demethanizer and/or deethanizer and other separating means for further separation of the individual components.

The liquid from the knock out tower 82, rich in propylene and propane is then withdrawn through a line 86 and pumped via a pump 88 through a line 90. A portion of the liquid in the line 90 can then be directed through a line 94 to combine with the line 60, as required, in a line 62 as a reflux liquid for the high pressure depropanizer 36. The other portion of the liquid in the line 90 can be directed through a line 96 to combine with a line 46 in a line 48 as a feed to the mixed phase hydrogenation reactor 54. Any excess liquid can be fed to the downstream separation system via a line 85.

Figure 2:
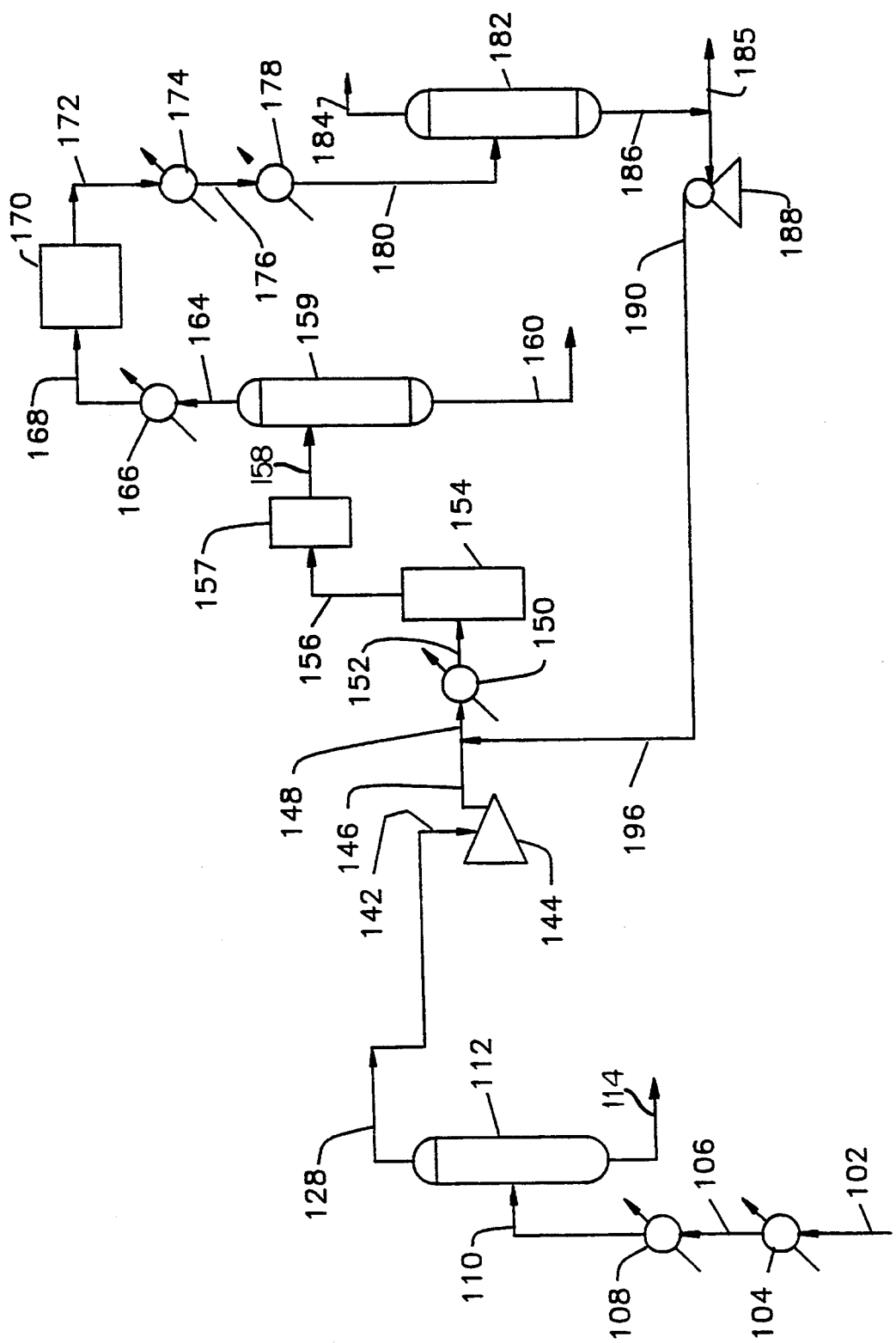
FIG. 2 depicts in flow chart format another embodiment of the present invention.

Many variations of the present invention will suggest themselves to those skilled in the art in light of the above-detailed description. For example, any of the known hydrogenation catalysts can be employed. Further, the reactor can be of the fixed bed type or other configurations useful in acetylene hydrogenation processes. Alternatively, it is also contemplated by the present invention that the mixed phase hydrogenation reactor can be employed in the front end of an olefins plant without a front end depropanizer. See FIG. 2 wherein for ease of understanding similar parts have been given similar reference characters to those set forth in FIG. 1. All such obvious modifications are within the full intended scope of the appended claims.

All of the above-referenced patents, patent applications and publications are hereby incorporated by reference.

We claim:

1. A process for hydrogenating acetylene in an olefin production plant, comprising the steps of, in sequence,
   (i) passing an olefin plant feedstream through a depropanizer to produce a liquid phase stream rich in $C_{4+}$ components and a vapor phase stream rich in $C_3$ and lighter components and comprising acetylene;
   (ii) cooling said vapor phase stream to form a mixed vapor-liquid stream and passing said mixed vapor-liquid stream through a mixed phase hydrogenation zone to selectively hydrogenate at least a portion of the acetylene in said vapor phase stream;
   (iii) separating the effluent from the mixed phase hydrogenation zone into a hydrogenated vapor stream and a hydrogenated liquid stream and passing said hydrogenated vapor stream to a vapor phase hydrogenation zone;
   (iv) passing the effluent from the vapor phase hydrogenation zone to zones of further separation; and
   (v) recycling said hydrogenated liquid stream to said depropanizer as a reflux for said depropanizer.

2. A process as defined in claim 1 wherein said olefin plant feedstream is derived from the product stream of a steam pyrolysis facility.

3. A process as defined in claim 1 wherein said olefin plant feedstream is derived from a catalytic cracking refinery off gas.

4. A process as defined in claim 1 wherein said olefin plant feedstream comprises butane, butenes, propane, propylene, ethane, ethylene, acetylene, methane, hydrogen, carbon monoxide and mixtures thereof.

5. A process as defined in claim 1 wherein said depropanizer operates at a high pressure ranging from about 150 psia to about 300 psia.

6. A process as defined in claim 1 wherein said mixed phase hydrogenation zone operates at a temperature of from about 10° C. to about 40° C. and a pressure of from about 200 psia to about 600 psia over a Group VIII metal hydrogenation catalyst.

7. A process as defined in claim 6 wherein said catalyst of the mixed phase hydrogenation is selected from the group consisting of Raney nickel, palladium-on-alumina, ruthenium-on-alumina, nickel arsenide-on-alumina and mixtures thereof.

8. A process as defined in claim 1 wherein said further separation zones comprise zones of demethanization, de-ethanization and combinations thereof.

9. A process as defined in claim 1 wherein said vapor phase hydrogenation is carried out over a catalyst comprising a Group VIII metal hydrogenation catalyst.

10. A process as defined in claim 9 wherein said vapor phase hydrogenation catalyst comprises a Group VIII metal in an amount ranging from about 0.01 to about 1 percent by weight of the total catalyst on a catalyst support.

11. A process as defined in claim 10 wherein said vapor phase hydrogenation catalyst is selected from the group consisting of Raney nickel, palladium-on-alumina, ruthenium-on-alumina, nickel arsenide-on-alumina mixtures thereof.

12. A process as defined in claim 10 wherein said vapor phase hydrogenation catalyst comprises a low surface area granular alumina impregnated with about 0.1 weight percent palladium.

13. A process as defined in claim 1 wherein said vapor phase hydrogenation zone is operated at a temperature in the range of about 10° C. to about 200° C. and a pressure in the range of about 200 psia to about 600 psia.

14. A process for hydrogenating acetylenes in an olefin production plant comprising the steps of:
   (a) passing an olefin containing feedstock through a chilling train to cool and at least partially condense said feedstock;
   (b) passing said cooled and partially condensed feedstock to a separation zone to produce a first liquid stream and a first vapor stream;
   (c) passing said first liquid stream to a lower end of a depropanizer;
   (d) passing said first vapor stream to an upper end of said depropanizer;
   (e) separating said first liquid stream and said first vapor stream in said depropanizer into a second liquid stream rich in $C_{4+}$ components and a second vapor stream rich in $C_3$ and lighter components, said depropanizer operating at a pressure ranging from 150 psia to 300 psia;
   (f) cooling and partially condensing said second vapor stream rich in $C_3$ and lighter components and passing said cooled and partially condensed stream to a mixed phase hydrogenation zone;
   (g) selectively hydrogenating at least a portion of acetylene in said mixed phase hydrogenation zone;
   (h) passing the effluent from said mixed phase hydrogenation zone in step (g) to a separation zone to separate said effluent into a third liquid stream and a third vapor stream;
   (i) recycling said third liquid stream to the top of the depropanizer as a reflux liquid;
   (j) passing said third vapor stream to a vapor phase hydrogenation zone to selectively hydrogenate substantially all of the remaining acetylene contained in said third vapor stream;
   (k) chilling and partially condensing the effluent from said vapor phase hydrogenation zone;
   (l) separating the chilled and partially condensed effluent from step (k) into a fourth liquid stream and a fourth vapor stream;
   (m) recycling said fourth liquid stream to either said depropanizer as a reflux liquid, or to said mixed phase hydrogenation zone as a feed stream; and
   (n) passing said fourth vapor stream to a downstream separation zone comprising a demethanizer, a de-ethanizer or a combination thereof.

15. A process for hydrogenating acetylenes in the front end of an olefin production plant comprising the steps of:
   (a) passing an olefin containing feedstock to a mixed phase hydrogenation zone to selectively hydrogenate at least a portion of the acetylene in said olefin containing feedstock;
   (b) passing the effluent from step (a) to a vapor phase hydrogenation reactor to selectively hydrogenate substantially all of the remaining acetylene in said effluent to form a second effluent;

(c) chilling and partially condensing said second effluent from step (b) to form a vapor phase and a liquid phase;

(d) separating said vapor phase and said liquid phase; and (e) recycling at least a portion of said liquid phase to said mixed phase hydrogenation zone.

16. A process for hydrogenating acetylene in an olefin production plant comprising the steps of:

(i) separating an olefin plant feedstream in a depropanizer to produce a liquid phase stream rich in $C_{4+}$ components and a vapor phase stream rich in $C_3$ and lighter components and comprising acetylene;

(ii) combining said vapor phase stream from step (i) with a second hydrogenated liquid stream to form a mixed phase stream;

(iii) selectively hydrogenating a portion of the acetylene in said mixed phase stream in a mixed phase hydrogenation zone to form a first hydrogenated mixed phase stream;

(iv) separating said first hydrogenated mixed phase stream into a first hydrogenated vapor stream and a first hydrogenated liquid stream;

(v) selectively hydrogenating at least a portion of the remaining acetylene in said first hydrogenated vapor stream to form a second hydrogenated vapor stream;

(vi) cooling and partially condensing said second hydrogenated vapor stream to form a second hydrogenated mixed phase stream;

(vii) separating said second hydrogenated mixed phase stream into a second hydrogenated vapor stream and said second hydrogenated liquid stream;

(viii) recycling said second hydrogenated liquid stream to step (ii); and (ix) recycling said first hydrogenated liquid stream to said depropanizer as reflux for said depropanizer.

* * * * *